United States Patent [19]

Kanamaru et al.

[11] Patent Number: 4,803,275
[45] Date of Patent: Feb. 7, 1989

[54] 2-OXO-5-METHYL-6-[4-HEPTENE]-2H-PYRANO[3,2-C]PYRIDINE

[75] Inventors: Tsuneo Kanamaru; Susumu Shinagawa; Masayuki Muroi, all of Osaka, Japan

[73] Assignee: Takeda Chemical Industries, Ltd., Japan

[21] Appl. No.: 92,310

[22] Filed: Sep. 2, 1987

[30] Foreign Application Priority Data

Sep. 11, 1986 [JP] Japan .................................. 61-215074

[51] Int. Cl.$^4$ .......................................... C07D 471/02
[52] U.S. Cl. .................................................. 546/116
[58] Field of Search ........................................ 546/116

[56] References Cited

PUBLICATIONS

Otto S. Wolfbeis, Monatshefte für Chemie, 113, pp. 365–370, (1982).

Primary Examiner—Alan L. Rotman
Assistant Examiner—Robert C. Whittenbaugh
Attorney, Agent, or Firm—Wegner & Bretschneider

[57] ABSTRACT

The present invention relates to a compound FA-4283 or its derivative of the formula:

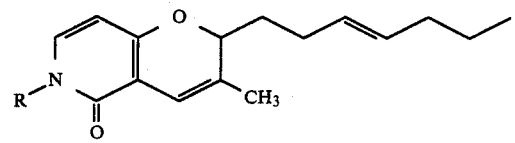

wherein R is hydrogen or lower alkyl, and 3,4- and 3',4'-double bond may be saturated with hydrogens, and the method of production thereof.

The compound (I) of the invention has an action of inhibiting fatty acid synthesis, thus being useful as an agent for prophylaxis and improvement of disorders of glucose and lipid methabolism.

8 Claims, 2 Drawing Sheets

2-OXO-5-METHYL-6-[4-HEPTENE]-2H-PYRANO[3,2-C]PYRIDINE

This invention relates to a novel physiologically active substance FA-4283, its derivatives and a method of producing same.

Obesity is caused by excessive accumulation of fat in adipose tissues, and it is well known that obesity is often associated with the so-called adult diseases such as diabetes, hyperlipemia, cardiovascular diseases and arthritis. It has been elucidated that these diseases are caused, directly or indirectly, by excessive accumulation of fat. Therefore, it is considered that these diseases can be cured and prevented by inhibiting the biosynthesis of fat and decreasing the fat-accumulation.

For the purpose of developing a novel agent capable of improving disorders of glucose and lipid metabolism including obesity, type II diabetes, and hyperlipemia accompanied by such conditions, the present inventors diligently conducted research for finding a substance capable of inhibiting synthesis of fatty acids in metabolites of microorganisms. As a result, they detected, in the culture broth of a microorganism belonging to the genus Penicillium, a substance capable of inhibiting synthesis of fatty acid, isolated this substance, and found that the substance was a novel one having an excellent activity of inhibiting synthesis of fatty acid. Based on this finding, the present inventors have further conducted research work to complete the present invention.

The present invention is to provide a compound FA-4283 or its derivative of the formula:

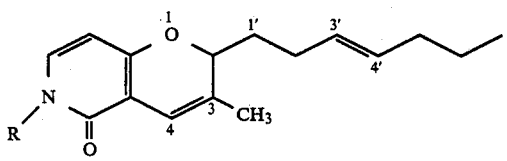

(I)

wherein R is hydrogen or lower alkyl and 3,4- and 3',4'-double bonds may be saturated with hydrogens, and a method of producing the compound (I) which comprises cultivating a microorganism belonging to the genus Penicillium capable of producing the compound FA-4283 in a culture medium, accumulating said FA-4283 in the culture broth, and then recovering the same, and if desired, alkylating or/and hydrogenating the resulting FA-4283.

Referring to compound (I), lower alkyl as R is preferably $C_{1-3}$ alkyl. R is most preferably hydrogen or methyl.

3,4-carbon atoms and 3',4'-carbon atoms in compound (I) may be connected by the respective double bonds or said 3,4- and 3',4'-double bonds may be saturated with hydrogens.

As microorganisms employable for the present invention, use is made of any ones belonging to the genus Penicillium and capable of producing physiologically active FA-4283. As a specific example serves the strain No. 4283 belonging to fungi, which was isolated from grassy soil at Gamagoori City, Aichi Prefecture, Japan, whose microbiological properties are as follows:

Cultural characteristics
(1) Malt Extract Agar

Abundant growth, colonies attaining a diameter of 5.0 to 6.0 cm after two weeks at 24° C., a colony surface funiculose with a slightly raised center, and with thin, regular margin. Good formation of aerial hyphae and conidia. The color of the growth was yellowish green to dark green in center, bright yellowish green in margin. Upper part of aerial hyphae showed pale brown. Reverse color was pale yellowish brown to dark brown. No production of soluble pigment.

(2) Potato-Glucose Agar

Abundant growth, colonies attaining a diameter of 4.2 to 5.0 cm after 2 weeks at 24° C. A colony surface funiculose with a slightly raised center, often showing aerial ropes of hyphae, with regular margin. Good formation of aerial hyphae and conidia. The color of the growth was pale brown to dark green in center and yellowish green in margin. On the surface of aerial hypae are deposited water droplets. Reverse color was pale yellowish brown to reddish brown. As the culture aged, pale red soluble pigment was produced slightly. Good growth at pH 3 to 10. Temperature range for growth was from 14° C. to 37° C., optimum temperature from 20° C. to 32° C. No growth at 39° C.

(3) Czapek's Agar

Moderate growth, colonies attaining a diameter of 3.2 to 4.0 cm after 2 weeks at 24° C. A tough mycelial felt with a slightly raised center, and with slightly irregular wavy margin. Good growth of aerial hyphae. The color of the growth was pale reddish and brownish yellow in center and white in margin. Conidial heads were few. Reverse color was pale yellowish brown to reddish brown. No production of soluble pigment. Morphology:

Conidiophore; arising from funiculose hyphae. 100 to 200μ long and 2 to 3μ in diameter, with septa and a smooth wall. Often colored.

Penicilli; biverticillata and symmetrica, sometimes fractional.

Metulae; 7 to 10×1.7 to 2.2μ, 4 to 6 metulae in the verticil, closely parallel, cylindrical.

Phialides; 10 to 12×1.5 to 2.0μ, 4 to 6 phialides closely in the vertical on metulae, cyrindrical and tapering off.

Conidia; elliptical to subglobose, 1.5 to 2×2 to 2.5 with smooth walls. Formed phialo-type and chaind.

By referring the foregoing properties to the Identification Table described on p.51 of "Isolation of 'Fungi-Cultivation and Identification" authored by D. Malloch, translated by Shun-ichi Udagawa (Published by Ishiyaku Shuppan Co., Ltd., 1983), it is apparent that the present strain belongs to the genus Penicillium. By further reference to the properties of fungi belonging to the genus Penicillium described on "A Manual of the Penicillia" authored by K. B. Raper et al. (published by The Williams & Wilkins Company, 1949), the present strain is considered to be identical with *Penicillium funiculosum* in view of its belonging to Biverticillata-Symmetrica Section, no formation of perithecium and the state of mycelia and conidiospores on the colonies, thus the present strain has been identified as *Penicillium funiculosum* No. 4283. In comparative cultivation of the present strain and *Penicillium funiculosum* IFO 6585 strain, no difference was observed in their taxonomical properties.

The above-mentioned *Penicillium funiculosum* No. 4283 strain has been deposited at the foundation, Institute for Fermentation Osaka with the accession number IFO-32058 as from Aug. 29, 1986. The present strain has also been deposited at Fermentation Research Institute belonging to Agency of Industrial Science and Technology, Ministry of International Trade and Industry, Japan (FRI, located at 1-1-3, Yatabe-cho Higashi, Tsukuba-gun, Ibaragi-Prefecture, Japan) with the accession number FERM P-8966 as from Sept. 9, 1986, the deposit being converted to a deposit under the Budapest Treaty, has been stored at FRI under the accession number of FERM BP-1420.

Strains belonging to the genus Penicillium can cause mutation, as general properties of microorganisms, spontaneously or by using a mutagen.

Among various mutants caused by irradiation of, for example, X-rays, gamma-ray, ultraviolet rays, etc., monospore separation, treatment with various chemicals, cultivation on a culture medium containing a relevant chemical, or any other means, or even those obtained spontaneously, any ones which are capable of producing FA-4283 can be employed for the method of the present invention.

As a medium employable for the method of the present invention, either a solid one or a liquid one may be used, if only the medium contains nutrient sources utilizable by a strain then used. When the cultivation is conducted on a large scale, use of a liquid medium is preferable. The medium is suitably incorporated with assimilable carbon sources, digestible nitrogen sources, inorganic substances and traced nutrients. The carbon sources are exemplified by glucose, lactose, surcrose, maltose, dextrin, starch, glycerol, mannitol, sorbitol, fats and oils (e.g. soybean oil, olive oil, rice bran oil, sesame oil, lard oil, chicken oil, etc.) and various aliphatic acids (e.g. lauric acid, myristic acid, palmitic acid, stearic acid, oleic acid, etc.). As the nitrogen sources, use is made of, for example, meat extract, yeast extract, dry yeast, soybean powder, corn-steep liquor, peptone, cotton seed powder, blackstrap molasses, urea, ammonium salts (e.g. ammonium sulfate, ammonium chloride, ammonium nitrate, ammonium acetate, etc.), etc. Besides, use is further made of salts including sodium, potassium, calcium, magnesium, etc., metal salts such as those of iron, manganese, zinc, cobalt, nickel, etc., salts of phosphoric acid, boric acid, etc., salts of organic acids such as acetic acid, propionic acid, etc. Besides, amino acids (e.g. glutamic acid, aspartic acid, alanine, lysine, valine, methionine, proline, etc.), peptide (e.g. dipeptide, tripeptide, etc.), vitamins ((e.g. $B_1$, $B_2$, nicotinic acid, $B_{12}$, C, etc.), nucleic acids (e.g. purine, pyrimidine and derivatives thereof), etc. may be allowed to be incorporated. Needless to state, for the purpose of adjusting the pH of a culture medium, inorganic or organic acids, alkalis, buffering agents, etc. may be added, or as an anti-foaming agent, an adequate amount of fats and oils, surface-active agents, etc. may be added. Cultivation may be conducted by means of static culture, shake-culture or aerated culture under stirring, etc. Of course, for a large scale cultivation, submerged culture under aeration and stirring is desirable. Culture conditions are naturally variable with states or compositions of the culture medium, kinds of the strain, means of the cultivation, etc., but usually a temperature range of from about 15° C. to about 37° C. and an initial pH range of from about 3 to about 10 are preferably selected. Especially, a temperature range of from about 20° C. to about 32° C. is preferable in the middle stage of the cultivation, and the initial pH is preferably in a range of from about 4 to about 6. The culture period is also variable with the foregoing conditions, but it is preferable to conduct the culture until the concentration of the physiologically active substance reaches maximum. The period required for this object is usually in a range of about 2 to about 14 days.

As the FA-4283 thus produced exists in the culture filtrate and cells, it may be recovered by subjecting the culture broth to centrifuging or filtration to separate into the supernatant and cells, followed by refining from the supernatant and the cells, respectively, but it is more advantageous to refine directly from the culture broth after adding to the culture broth an organic solvent such as methanol.

For recovering the compound FA-4283 from the culture liquid, as the compound is a neutral fat-soluble substance, conventional means for recovering such metabolites of microorganisms can be usually resorted to conveniently. For example, a means utilizing the differnce of solubilities between the product and impurities, adsorption chromatography using various carriers such as activated charcoal, non-ionic high porous resin, silica gel, alumina, etc. can be employed independently or in a suitable combination.

For recovering the FA-4283 substance produced in the culture broth, firstly the cells and the supernatant of the culture broth are separated from each other by, for example, filtration, the resultants are respectively subjected to extraction with an organic solvent or, an organic solvent capable of dissolving the compound FA-4283 such as methanol, acetone, ethylacetate, etc. is directly added to the culture broth for extracting the compound by stirring to thereby obtain the substance.

As the organic solvent employable for extracting the said substance from the culture broth, culture filtrate or cells, use is made of, for example, fatty acid esters such as ethyl acetate, etc., alcohols such as butanol, etc., halogenated hydrocarbons such as chloroform, etc., ketones such as acetone, etc., etc. The extract solution containing the compound FA-4283 is purified by, after concentration, allowing to be adsorbed on an adsorbent such as silica gel, etc., then by developing with a suitable solvent.

When, as the adsorbent, silica gel (Merck, Kieselgel, etc.) for example is employed, as the developing solvent, is generally employed a combination of a polar organic solvent and a non-polar organic solvent, such as a mixture solvent of methanol and chloroform or methylene chloride, or of ethyl acetate and n-hexane. More specifically, the development is conducted first with a solvent mixture containing a non-polar solvent at a higher ratio, then, with solvent mixture whose content of polar solvent is increased gradually, elution is conducted to separate from impurities.

When the amount of impurities is relatively large, chromatography is repeated by suitably changing the combination of organic solvents to obtain refined compound FA-4283.

Physico-chemical properties of thus-procuced physiologically active substance FA-4283 are as shown below.

(1) Form: pale yellow crystalline solid matter
(2) m.p.: 75° C. to 95° C.
(3) Elemental Analysis %: C, 74.09, H, 8.27, N, 5.44
(4) Molecular weight: 259 (by mass spectrometry)
(5) Estimated molecular formula: $C_{16}H_{21}NO_2$
(6) Specific optical rotation: $[\alpha]_D^{22}$ 0° to +40° (c=1, ethanol)

(7) Ultraviolet absorption spectrum: the spectrum measured in methanol is as shown by FIG. 1, having maximum absorptions at 235 nm($E_{1cm}^{1\%}$810) and 330 nm ($E_{1cm}^{1\%}$350)

(8) Infrared absorption spectrum: the spectrum measured as KBr tablets is as shown in FIG. 2

(9) 13C-NMR spectrum: chemical shifts (δppm) measured in $CDCl_3$ are as follows: 13.4, 19.2, 22.4, 27.5, 32.6, 34.4, 79.0, 100.3, 107.8, 113.1, 128.6, 129.3, 131.0, 133.2, 160.5, 162.6

(10) Colour reaction:
- positive; phosphomolybdic acid, iodine reaction
  pseudo-positive; ninhydrin reaction
  negative: Sakaguchi reaction

(11) Solubility:
  insoluble; water
  sparingly soluble; petroleum ether, n-hexane
  soluble; ethyl acetate, diethyl ether
  readily soluble; chloroform, methanol, ethanol, dimethyl-formamide, dimethyl sulfoxide

(12) Thin-layer chromatography:
  silica gel plate (manufactured by Merck, Kieselgel 60$F_{254}$)
    solvent system; Rf
    chloroform-methanol (9:1); 0.29
    n-propanol-water (4:1); 0.70

In view of the physico-chemical properties as mentioned above, the compound FA-4283 is considered as a novel compound having a 2H-pyrano[3,2-c]pyridine skeleton of the formula:

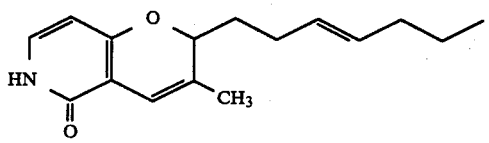

(II)

The compound FA-4283 suggests, in view of its structure, the existence of plural tautomers such as

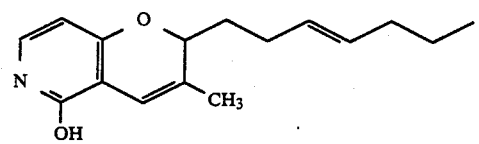

(III)

and, the physico-chemical properties are, as observed in the melting point, specific optical rotation, etc., indefinite in numerical values, varying with processes of production, purification, etc.

The compound FA-4283 may be converted to its derivatives by chemical modification, e.g. alkylation, hydrogenation etc.

These reactions may be conducted by use of organic solvent, such as alcohols (e.g. methanol, ethanol), ketones (e.g. acetone, methyl ethyl ketone) or the mixture of organic solvent and water.

The catalyst of inorganic base such as sodium salt (e.g. sodium carbonate) and potassium salt (e.g. potassium carbonate) may be used for the alkylation together with the alkylating agent such as alkylhalide (e.g. methyl iodide, ethyl iodide). The alkylation reaction may preferably conducted under heating (50°-100° C.).

The hydrogenation such as catalytic reduction may be conducted by use of catalyst, e.g. palladium-black, platinum oxide, and hydrogen gas. The hydrogenation is usually conducted at room temperature.

FA-4283 can be converted to its N-alkyl derivatives (R=lower alkyl) by alkylation and to its 3,4- and 3',4'-tetrahydro derivatives by hydrogenation.

The derivatives of FA-4283 may be purified by conventional manners such as extraction, column chromatography and recrystallization mentioned above.

Compound (I) of the present invention has an action of inhibiting the synthesis of fatty acid, which is less toxic and useful as, for example, an agent of preventing and improving disorders of glucose and lipid metabolism, glycolipid in mammals (e.g. mouse, rat, man).

When FA-4283 is used as, for example, an agent of improving disorders of glucose and lipid metabolism, glycolipid metabolic disorders including obesity, type II diabetes accompanied by obesity and hyperlipemia, the daily dosage is about 2 to 400 mg/kg for an adult. FA-4283 can be administered orally as, for example, tablets, granules, capsules, liquids, etc., or non-orally as, for example, injections, formulated by per se conventional means.

Compound (I) of the present invention can be used as a biochemical reagent for probing fatty acid metabolism in mammals, fungi and yeast.

EXAMPLES

Figure 1:
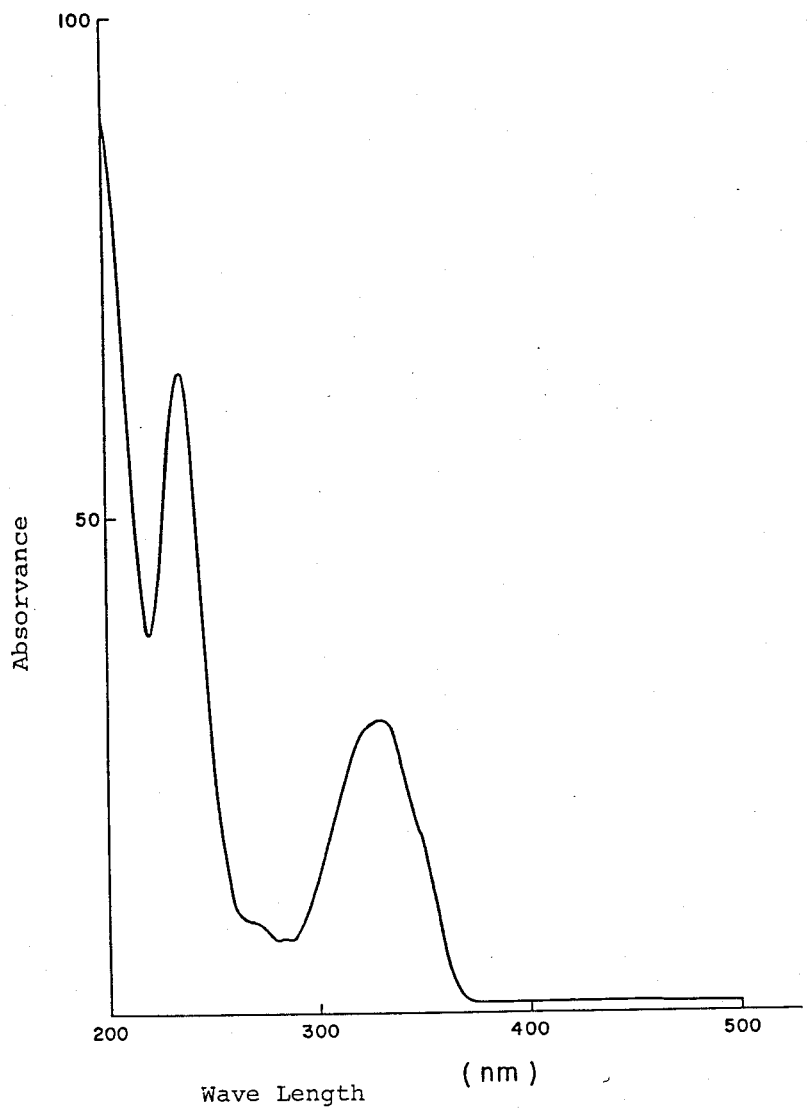
FIG. 1 and FIG. 2 show UV spectrum and IR spectrum of FA-4283, respectively.

The present invention is further illustrated specifically by the following experimental and working examples. In the working examples, percents for the components of the culture media are stated in weight by volume.

Experimental Example 1 (inhibitory activity of the Synthesis of Fatty Acid)

Determination of the Inhibitory activity of the synthesis of fatty acid was conducted by using homogenates prepared from rat livers. Preparation of the rat liver homogenates, composition of the reaction solution for determination of inhibitory activity and method of the determination were in accordance with the method by J. Iliffe et al. described on "Biochemical Journal" 91, 369 (1964) and the method by T. Kariya et al. described on "Biochemical and Biophysical Research Communications" 80, 1022 (1978). More specifically, SD-strain male rats (6-week old) had been fasted for 2 days and then refed for 24 hours. They were killed by blood letting. The livers were then removed immediately, to which was added a 0.25M sucrose solution containing 2 mM EDTA, 5 mM nicotinamide and 1 mM 2-mercaptoethanol so that the final volume of the solution may be 4 ml relative to 1 g of the wet weight of the livers. The mixture was homogenized in a homogenizer with a Teflon plunger. The homogenate was centrifuged at 700 g for 10 minutes, and the supernatant was decanted and 0.5 ml thereof was used as the standard sample of enzyme.

Into a 10 ml flask containing 1.85 ml of a reaction mixture consisting of 45 mM of tris-HCl buffer (pH 7.4), 10 mM of $KHCO_3$, 4 mM of $MgCl_2$, 45 mM of KCl, 5 mM of $K_2HPO_4$, 15 mM of potassium citrate, 1 mM of NADP, 2 mM of ATP, 5 mM of glucose-6-phosphate, 0.4 mM of coenzyme A, 5 mM of dithiothreitol and 0.5 ml of the enzyle solution, was blown a mixture gas (95% $O_2$:5% $CO_2$). Then the flask was tightly stoppered and kept at 37° C. for 60 minutes under gentle shaking. Then, to the flask were added 0.5 mM of 1-$^{14}C$-acetate (0.2 μCi) and 50 μl of methanol or a methanol solution containing the subject compound, and the reaction was allowed to proceed at 37° C. for 60 minutes while shaking gently. One ml of the reaction solution was taken and subjected to alkali hydrolysis in KOH-ethanol. To the hydrolyzate was added hydrochloric acid to render it to be acid, and it was subjected to extraction with petroleum ether, followed by washing with water. The radio-activity extracted into the petroleum ether layer was measured. The inhibitory activity of the compound FA-4283 was 97% at $5 \times 10^{-4}M$ as compared with the case of no addition of the inhibiting agent, while 98% inhibition was observed at $10^{-3}M$.

Experimental Example 2

Antibacterial spectrum of the physiologically active substance FA-4283 is as shown in Table 1.

TABLE 1

| Antimicrobial activity of FA-4283 | |
| --- | --- |
| Microorganism | Minimum Inhibitory Concentration (MIC; μg/ml) |
| Escherichia coli K 12 | >100 |
| Proteus vulgaris IFO 3045 | >100 |
| Pseudomonas aeruginosa IFO 3080 | >100 |
| Staphylococcus aureus FDA 209 P | >100 |
| Bacillus subtilis PCI 219 | >100 |
| Bacillus cereus IFO 3514 | >100 |
| Candida albicans IFO 0583 | 3.13 |
| Candida krusei IFO 1395 | >100 |
| Candida parakrusei IFO 0640 | >100 |
| Candida utilis IFO 0619 | 3.13 |
| Candida parapsilosis IFO 1396 | >100 |
| Candida tropicalis IFO 0006 | 50 |
| Saccharomyces cerevisiae IFO 0209 | >100 |
| Rhodotorula rubra IFO 0907 | 0.39 |
| Cryptococcus neoformans IFO 0410 | 25 |
| Penicillium chrysogenum IFO 4626 | >100 |
| Aspergillus niger IFO 4066 | >100 |
| Trichophyton mentagrophytes IFO 7522 | 6.25 |
| Trichophyton rubrum IFO 5467 | 6.25 |
| Pyricularia oryzae P-18 | 3.18 |

TSA* medium containing 1% glucose was used.
TSA*: Trypticase Soy Agar (manufactured by BBL Microbiology Systems)

These experimental results suggest that the compound FA-4283 shows its antimicrobial activity against yeasts and fungi and its utilizability as antifungal and anti-yeast agent. Furthermore, the compound FA-4283 is also useful as an intermediate for synthesizing a compound showing an advantageous activity of inhibiting the synthesis of fatty acid or a compound showing a stronger anti-fungal and anti-yeast activity as well as other physiologically active substances.

Incidentally, the acute toxicity $LD_{50}$ of FA-4283 was not less than 400 mg/kg by a single dose at intraperitoneal administration in mice.

Example 1

One loopful of *Penicillium funiculosum* No. 4283 sufficiently sporulate on a potato.sucrose-agar slant was used to inoculate a sterilized 2 l of Sakaguchi flask containing 500 ml of a seed culture medium (pH 6.0) composed of 2.0% glucose, 3.0% maltose, 1.5% raw soybean meal, 1.0% corn-steep liquor, 0.5% polypepton, 0.3% yeast extract and 0.3% common salt. Thus-inoculated medium was incubated at 28° C. for two days on a reciprocal shaker. A 500 ml portion of the inoculum thus obtained was transferred to a sterilized 50 l fermentation vessel containing 30 l of the above-mentioned seed culture medium, which was incubated at 28° C. for two days by stirring under aeration. A 5 l portion of the culture broth thus obtained was transplanted on 100 l of a main culture medium (pH 4.5) composed of 1% glucose, 4% dextrin, 0.5% raw soybean meal, 0.5% maltose extract, 0.5% polypepton, 0.2% yeast extract, 0.05% $FeSO_4.7H_2O$, 0.05% $MgSO_4.7H_2O$ and 0.1% $KH_2PO_4$ contained in a sterilized 200 l fermentation vessel, which was incubated for 4 days at 28° C., 1.0 kg/cm$^2$ internal pressure, 100 l/min. aeration and 200 r.p.m agitation.

Example 2

To 85 l of the culture broth obtained in Example 1 was added 170 l of methanol, and the mixture was stirred for one hour. The resultant was subjected to filtration to remove cells, and the filtrate was concentrated under reduced pressure to a volume of 22 l. The concentrate was subjected to extraction twice with 11 l each portion of ethyl acetate. The extracts were combined, washed with 10 l of 2% sodium hydrogencarbonate and 10 l of water in sequence, followed by concentration under reduced pressure to give an oily product. This oily product was allowed to be adsorbed on a column of 600 g of silica gel (Kieselgel 60, Merck). The column was developed with 3 l of dichloromethane and 4.5 l of methanol dichloromethane (2:98) in sequence. Active fractions were combined and concentrated to obtain an oily product, which was again allowed to be adsorbed on a column of 600 g of silica gel (Kieselgel 60, Merck), followed by developing with 6 l of chloroform, 3 l of methanol-chloroform (1:99) and 4.5 l of methanol-chloroform (2:98). Active fractions were combined and concentrated under reduced pressure to obtain 31 g of an oily product. This oily product was allowed to be adsorbed on a column of 500 g of silica gel, and the column was developed wtih 14 l of dichloromethane, 3 l of methanol-dichloromethane (1:99) and 10 l of methanol-dichloromethane (3:197) in sequence. Active fractions were combined and concentrated under reduced pressure to obtain an oil product, which was crystallized from petroleum benzin to obtain 6.2 of crude crystals. Recrystallization from petroleum benzin gave 4.6 g of the substance FA-4283, m.p. 79°–80° C. $^1H$-NMR 90 MHz (in $CDCl_3+D_2O$, δ ppm): 0.86(3H, t), 1.35(2H, sext.), 1.6 to 2.3(6H, m), 1.81(3H, s), 4.77(1H, dd), 5.44(2H, m), 5.95(1H, d) 6.40(1H, s), 7.17(1H, d).

Specific optical rotation $[\alpha]_D^{22}+38.3°$ (c=1, EtOH).
Elementary Analysis (%): Experimental Value: C; 74.23, H; 8.23, N; 5.36.

Figure 2:
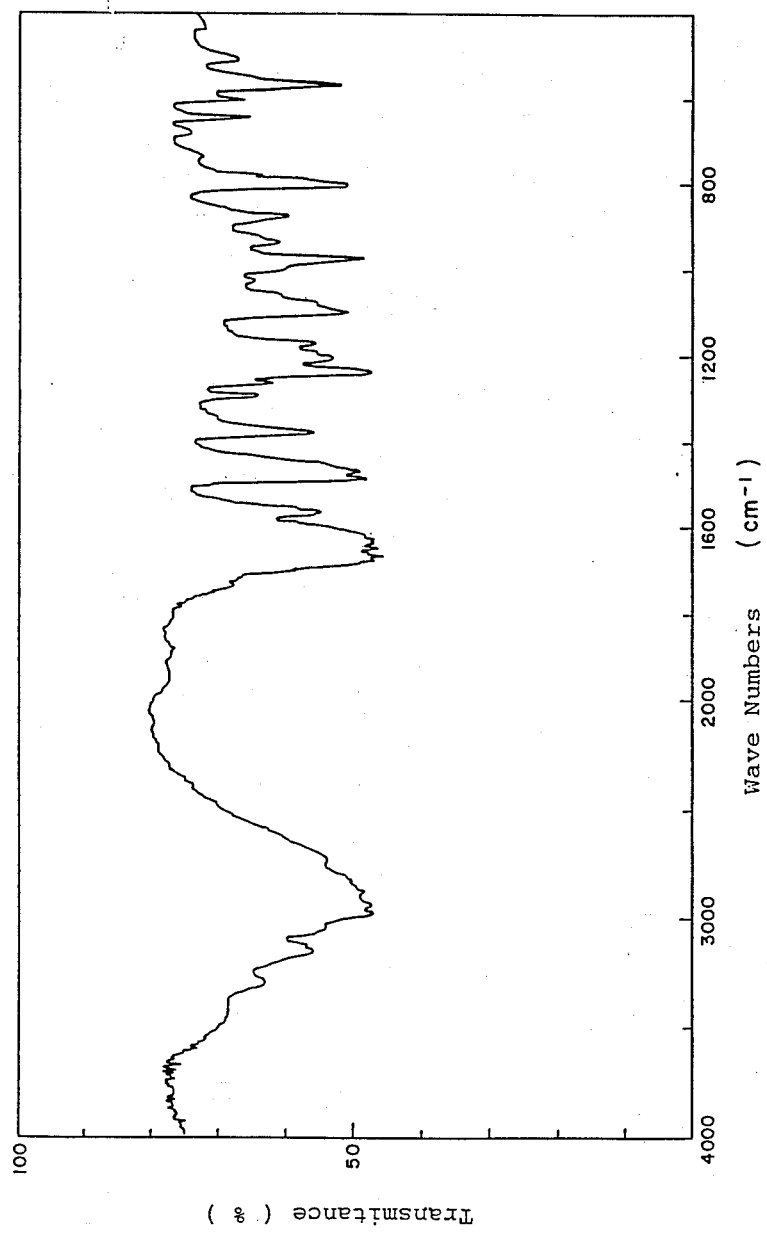

Ultraviolet absorption spectrum and infrared absorption spectrum are shown by FIG. 1 and FIG. 2.

Example 3

To 80 l of a culture broth of a strain of *Penicillium funiculosum* No. 4283, which was obtained by the procedure of Example 1, was added 160 l of methanol, and the mixture was stirred for one hour. The resultant was subjected to filtration to remove cells, and the filtrate was concentrated under reduced pressure to a volume of 23 l. The concentrate was subjected to extraction twice with 14 l of ethyl acetate. The extract solutions were combined and washed with 14 l of 2% sodium hydrogencarbonate and 13 l of water in sequence, followed by concentration under reduced pressure to obtain an oily product. This oily product was allowed to be adsorbed on a column of 1 kg of silica gel (Kieselgel 60, Merck). The column was developed with 15 l of dichloromethane, 10 l of methanol-dichloromethane (1:99) and 5 l of methanol-dichloromethane (3:197) in sequence. Active fractions were concentrated to give an oily product, which was again allowed to be adsorbed on a column of 500 g of silica gel (Kieselgel 60, Merck), followed by developing with 8 l of dichloromethane, 5 l of methanol-dichloromethane (1:99) and 10 l of methanol-dichloromethane (3:197). Active fractions were combined and concentrated to give an oily product. This oily product was allowed to be adsorbed on a column of 250 g of silica gel, followed by developing with 7 l of dichloromethane, 3 l of methanol-dichloromethane (1:99) and 4 l of methanol-dichloromethane (3:197) in sequence. Active fractions were combined and concentrated to give an oily product, which was crystallized from petroleum benzin to give 2.9 g of crude crystals. Recrystallization from ethyl acetate-petroleum benzin gave 1.0 g of pale yellow crystals, m.p. 83°–85° C. $[\alpha]_D^{24}+21.6°$ (c=1, EtOH).

Elemental Analysis (%): Experimental Value: C; 74.01, H; 8.04, N; 5.44.

Example 4

To 80 l of a culture broth of a strain of *Penicillium funiculosum* No. 4283, which was obtained by a procedure like that in Example 1, was added 160 l of methanol, and the mixture was stirred for one hour. The resultant was subjected to filtration to remove cells, and the filtrate was concentrated under reduced pressure to a volume of 25 l. The concentrate was subjected to extraction twice with 13 l of ethyl acetate. The extract solutions were combined and washed with 13 l of 2% sodium hydrogencarbonate and 12 l of water in sequence, followed by concentration under reduced pressure to give an oily product. This oily product was allowed to be adsorbed on a column of 1 kg of silica gel (Kieselgel 60, Merck). The column was developed with 16 l of dichloromethane, 16 l of methanol-dichloromethane (1:199), 6 l of methanol-dichloromethane (1:99) and 8 l of methanol-dichloromethane (3:197) in sequence. Active fractions were combined and concentrated to give an oily product, which was crystallized from petroleum benzin to give 4.5 g of crude crystals. The crude crystals were again allowed to be adsorbed on a column of 60 g of silica gel, followed by developing with 200 ml of dichloromethane, 800 ml of methanol-dichloromethane (1:199) and 500 ml of methanol-dichloromethane (1:99) in sequence. Active fractions were combined and concentrated to give a crystalline product, which was recrystallized from petroleum benzin to give 2.2 g of a pale yellow crystals, m.p. 85°–87° C. $[\alpha]_D^{24}+17.3°$ (c=0.9, EtOH).

Elemental Analysis (%): Experimental Value: C; 73.51, H; 8.06, N; 5.73

Example 5

Oily products recovered from the mother liquors resulting from crystallization from petroleum benzin performed in Example 3 and 4 were combined (18.0 g) were allowed to be adsorbed on 150 g of silica gel, followed by developing with 2 l of chloroform and 1.5 l of methanol-chloroform (1:199) in sequence. Active fractions were combined and concentrated, followed by crystallization from petroleum benzin to give 3.5 g of crude crystals. Recrystallization from petroleum benzin gave 2.7 g of pale yellow crystals, m.p. 89°–91° C. $[\alpha]_D^{23}+6.6°$ (c=0.8, EtOH).

Elemental Analysis (%): Experimental Value: C; 74.11, H; 8.24, N; 5.41.

Example 6

FA-4283 (500 mg) was dissolved in a mixture solvent of methanol (80 ml) and water (20 ml). The resulting solution was subjected to the catalytic hydrogenetion in the presence of Palladium-black (1 g) at atmospheric pressure. The catalyst was filtered off and the filtrate was concentrated under reduced pressure. Water (30 ml) and ethyl acetate (50 ml) was added to the resulting residue. The ethyl acetate layer obtained was dried over anhydrous Na$_2$SO$_4$ and concentrated under reduced pressure. The resulting residue was crystallized from petroleum benzin and then recrystallized from petroleum benzin to give 3,4,3',4'-tetrahydro FA-4283 as colorless crystals (250 mg). mp. 100°–101° C. $[\alpha]_D^{25}+3.8°$ (C=0.5, EtOH). SI-MS: m/z 264 (M+1).

Elemental Analysis (%): Calcd. for C$_{16}$H$_{25}$NO$_2$; C: 72.97, H: 9.57, N: 5.32 Found; C: 72.96, H: 9.63, N: 5.33.

PMR (400 MHz, in CDCl$_3$, δ): 0.89 (t, 3H), 0.94 (d, 3H), 1.30 (m, 10H), 1.49 (m, 1H), 1.65 (m, 1H), 2.15 (m, 1H), 2.35 (dd, 1H), 2.64 (dd, 1H), 4.05 (m, 1H), 5.97 (d, 1H), 7.23 (d, 1H), 12.49 (bs, 1H).

Example 7

To the solution of FA-4283 (500 mg) in acetone (50 ml), was added anhydrous potassium carbonate (2.0 g) and methyl iodide (0.3 ml). The reaction mixture was heated for 10 hours under reflux. The insolubles were filtered off and the filtrate was concentrated under reduced pressure. Ethyl acetate (50 ml) and 5% aqueous NaHCO$_3$ (50 ml) was added to the resulting residue. The ethyl acetate layer was washed with 5% aqueous citric acid and with water, and then dried over anhydrous NaHCO$_3$. The ethyl acetate was distilled off under reduced pressure to obtain an oil (600 mg). The resulting oil was purified by column chromatography using 11 g of silica gel (developing solvent: chloroform). The fractions showing a single spot on TLC were collected and concentrated to obtain N-methyl FA-4283 (410 mg) as an oil. $[\alpha]_D^{25}+4°$ (C=0.69, in ethanol) EI-MS: m/z 273 (M+)

Elemental Analysis (%): Calcd. for C$_{17}$H$_{23}$NO$_2$0.2-H$_2$O; C: 73.72, H: 8.51, N: 5.06 Found; C: 73.86, H: 8.41, N: 4.77

PMR (100 MHz, in CDCl$_3$, δ value for main peaks): 0.88 (t, 3H), 1.36 (sext., 2H), 1.80 (bs, 3H), 3.47 (s, 3H), 4.72 (dd, 1H), 5.43 (m, 2H), 5.85 (d, 1H), 6.45 (bs, 1H), 7.03 (d, 1H).

What is claimed is:

1. A compound of the formula:

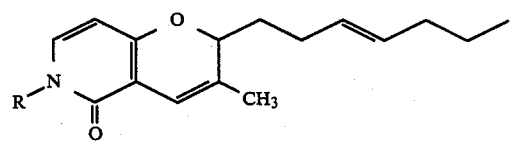

wherein R is hydrogen or lower alkyl and 3,4- and 3',4'-double bonds may be saturated with hydrogens.

2. The compound according to claim 1, wherein R is hydrogen.

3. The compound according to claim 1, wherein R is $C_{1-3}$ alkyl.

4. The compound according to claim 3, wherein R is methyl.

5. The compound according to claim 1, wherein 3,4-carbon atoms and 3',4'-carbon atoms are connected by the respective double bonds.

6. The compound according to claim 1, wherein R is hydrogen and 3,4-carbon atoms and 3',4'-carbon atoms are connected by the respective double bonds namely FA-4283.

7. The compound according to claim 1, wherein R is methyl and 3,4-carbon atoms and 3',4'-carbon atoms are connected by the respective double bonds.

8. The compound according to claim 1, wherein R is hydrogen and 3,4-carbon atoms and 3',4'-carbon atoms are saturated with hydrogens. the genus Penicillium capable of producing the compound FA-4283 in a culture medium, accumulating said FA-4283 in the culture broth, and then recovering the same, and if desired, alkylating or/and hydrogenating the resulting FA-4283.

* * * * *